United States Patent [19]

Albert

[11] 4,048,496

[45] Sept. 13, 1977

[54] SELECTABLE WAVELENGTH X-RAY SOURCE, SPECTROMETER AND ASSAY METHOD

[76] Inventor: Richard D. Albert, 317 Hartford Drive, Danville, Calif. 94526

[21] Appl. No.: 633,980

[22] Filed: Nov. 20, 1975

Related U.S. Application Data

[63] Continuation-in-part of Ser. No. 353,451, April 24, 1973, Pat. No. 3,925,660, which is a continuation-in-part of Ser. No. 251,378, May 8, 1972, abandoned.

[51] Int. Cl.² .............................................. G01N 23/20
[52] U.S. Cl. ..................................... 250/272; 250/273
[58] Field of Search ........................ 250/272, 273, 311

[56] References Cited

U.S. PATENT DOCUMENTS

| 2,925,497 | 2/1960 | Bessen | 250/272 |
|---|---|---|---|
| 3,525,863 | 8/1970 | Constantine et al. | 250/272 |
| 3,671,744 | 6/1972 | Constantine | 250/272 |
| 3,766,383 | 10/1973 | Harris | 250/272 |
| 3,920,984 | 11/1975 | Kirkendall et al. | 250/272 |

FOREIGN PATENT DOCUMENTS

| 1,219,448 | 1/1971 | United Kingdom | 250/272 |

OTHER PUBLICATIONS

"Sourcebook on Atomic Energy", Ch. IV, The Structure of the Atom, pp. 111-113, 1958.

*Primary Examiner*—Harold A. Dixon
*Attorney, Agent, or Firm*—Phillips, Moore, Weissenberger, Lempio & Majestic

[57] ABSTRACT

A method and apparatus for producing X-rays having any selected one of a plurality of specific different wavelength spectra greatly facilitates X-ray fluorescence analysis of samples to detect constituent elements. In the X-ray source, an electron beam is directed to any selectable one of an array of primary targets of different composition. X-rays from the selected primary target may be utilized directly or caused to impinge on any selected one of a plurality of secondary targets, which are also each of differing composition to cause the secondary target to emit a specific X-ray spectrum characteristic of that secondary target. Analysis of the X-ray fluorescence from a sample irradiated by a plurality of different specific selected X-ray spectra enables identification and measurement of particular chemical elements in the sample. The system including the selection of appropriate combinations of primary and secondary targets may be uncontrolled manually or by a computer responsive to the detector of the X-ray fluorescence from the sample.

3 Claims, 9 Drawing Figures

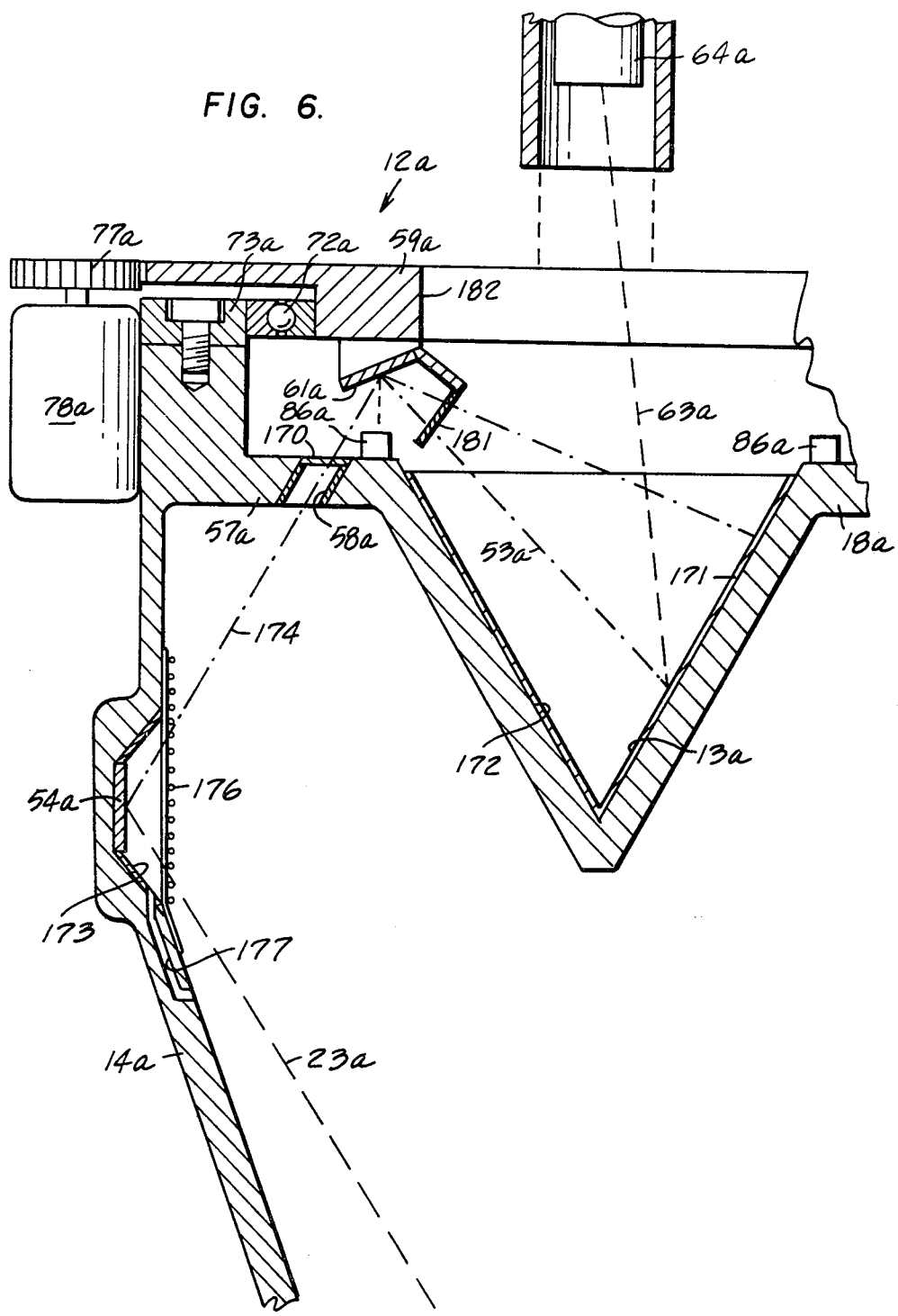

SELECTABLE WAVELENGTH X-RAY SOURCE, SPECTROMETER AND ASSAY METHOD

CROSS-REFERENCE TO RELATED APPLICATIONS

This application is a continuation of prior copending application Ser. No. 353,451 (now United States Patent 3,925,660) of Richard D. Albert filed Apr. 24, 1973 for SELECTABLE WAVELENGTH X-RAY SPECTROMETER AND ASSAY METHOD, said application Ser. No. 353,451 having been a continuation-in-part of prior application Ser. No. 251,378 of Richard D. Albert, filed May 8, 1972, for SELECTABLE WAVELENGTH X-RAY SPECTROMETER AND ASSAY METHOD, now abandoned. Copending application Ser. No. 537,072, filed Dec. 30, 1974 by Richard D. Albert (now U.S. Pat. No. 3,983,397) is a divisional application of said application Ser. No. 353,451.

BACKGROUND OF THE INVENTION

This invention relates to a method and apparatus for producing X-rays of selectable wavelengths and intensities and to a system utilizing such X-rays to detect specific chemical elements in a sample by analysis of X-ray fluorescence therefrom.

When exposed to X-rays, most substances will fluoresce X-rays that have a specific wavelength or combination of specific wavelengths that are characteristic of the chemical elements in the substance. The wavelength spectrum of the X-ray fluorescence is not determined by that of the incident X-rays which are causing the fluorescence but is instead determined by the elemental composition of the substance. As the fluorescent X-ray spectrum is distinct for each different element, this offers a technique for rapidly and nondestructively detecting the presence of a specific element in a sample or for identifying the total chemical composition of the sample. The complete fluorescent X-ray spectrum of an unknown substance provides a fingerprint for that substance which contains all the information needed to identify and quantitatively analyze most of the elements that may be present in the substance.

This technique has heretofore been used only on a very limited basis, mostly within the confines of research laboratories, to analyze specific substances for specific elements using an assembly of devices useful only for that particular analysis. One major problem is that conventional X-ray tubes or sources are not easily controllable with respect to the wavelength spectrum which is produced. The conventional X-ray tube consists of means for accelerating a beam of electrons toward a target or anode generally composed of a refractory metal such as tungsten or the like. The resultant X-rays have two principal components. One consists of the characteristic X-ray fluorescence wavelengths of the target material and the other is a polychromatic spectrum known as bremmstrahlung which contains a more or less continuous distribution of wavelengths. The characteristic specific wavelength of the target material is unchangeable and is accompanied by a heterogeneous mixture of many wavelengths. Use of such an X-ray tube complicates the X-ray fluorescence analysis technique described above and greatly limits the accuracy of the result. While, as pointed out above, the wavelength of X-ray fluorescence from a sample is not determined by the wavelength of the incident X-rays, this does not mean that control of the wavelength of the incident X-rays is unimportant. First, the intensity of the X-ray fluorescence from the sample is strongly dependent upon the wavelength of the incident X-rays. Second, the presence of the bremmstrahlung spectrum in the vicinity of the sample can greatly interfere with detection of the desired sample fluorescence.

Accordingly, efficient use of the X-ray fluorescence analysis technique requires a substantially bremmstrahlung-free source of X-rays having a specific wavelength spectrum. Further, if the technique is to be used to analyze a sample for a variety of initially unknown possible chemical element constituents, the source of X-rays should be readily adjustable to produce any selected one of a large number of specific wavelengths or wavelength spectra since it may be necessary to sequentially irradiate the sample with a series of different wavelengths to produce a strong fluorescence response from each of the various constituent elements. This change of output wavelengths should be accomplishable quickly and by a simple adjustment of controls either manually or preferably by an automatic feedback system which responds to the sample X-rays fluorescence. These objectives cannot be accomplished if the X-ray source apparatus must be disassembled and reconstructed in part to produce a desired specific wavelength spectra.

Moreover, an X-ray source producing selectable wavelengths and intensities can offer important advantages in contexts other than the spectrometric analysis of substances as discussed above. In radiology as used for medical purposes or for the inspection of industrial parts, for example, the image which is obtained of the internal structure of a subject is useful only to the extent that different internal elements of the subject are distinguishable in the image. The contrast in such an image, between different internal areas of the subject, is again strongly influenced by the wavelength of the incident X-rays. The particular wavelength which provides the best contrast in an image of a medical patient between bone structure and the surrounding soft tissue may not be the same wavelength which provides the best contrast in distinguishing tumorous tissue from adjacent normal tissue. Thus, the versatility of radiology equipment of this kind may also be greatly enhanced by an X-ray source providing for selection of any of a plurality of different wavelength spectra.

SUMMARY OF THE INVENTION

This invention provides for a rapid, efficient and accurate detection of constituent elements in a sample by X-ray fluorescence analysis. An X-ray source, also usable for purposes additional to sample analysis, is provided for generating any selected one of a plurality of different wavelength spectra which may include substantially monochromatic spectra. Selection of the wavelength and intensity of the output of the source is readily accomplished by manual adjustment of controls or, in one preferred form, by a feedback system responsive to detected X-ray fluorescence from the sample.

Within the X-ray source, an electron beam or the like is controllably directable to any of an array of primary targets of different composition. In a preferred form, primary X-rays emitted from the selected primary target may be selectively transmitted directly to the sample or caused to impinge upon any selectable one of an array of secondary targets which are also each of different composition. The resultant X-ray emission from the selected secondary target has a spectrum determined by that particular target and is transmitted to the sample or the like, means being provided for suppressing bremmstrahlung which might otherwise reach the sample. The invention includes a number of additional novel features which will hereinafter be described in connection with the description of preferred embodiments.

Accordingly, it is an object of this invention to facilitate the detection and measurement of constituent elements in a substance by analysis of X-ray fluorescence therefrom.

It is another object of this invention to provide a method and apparatus for producing X-rays having any selected one of a plurality of predetermined wavelength spectra and intensities.

It is still another object of this invention to provide for the automatic cycling of output of X-ray wavelengths and intensities in an X-ray source to facilitate assay of a sample by analysis of fluorescent X-rays emitted therefrom.

Still another object of the invention is to provide for the suppression of bremmstrahlung in an X-ray source capable of producing any of a plurality of specific predetermined X-ray wavelengths.

The invention, together with further objects and advantages thereof, will best be understood by reference to the following description of certain preferred embodiments taken in conjunction with the accompanying drawings.

BRIEF DESCRIPTION OF THE DRAWINGS

In the accompanying drawings:

FIG. 6 illustrates a modified construction of the X-ray source;

DESCRIPTION OF PREFERRED EMBODIMENTS

Figure 1:
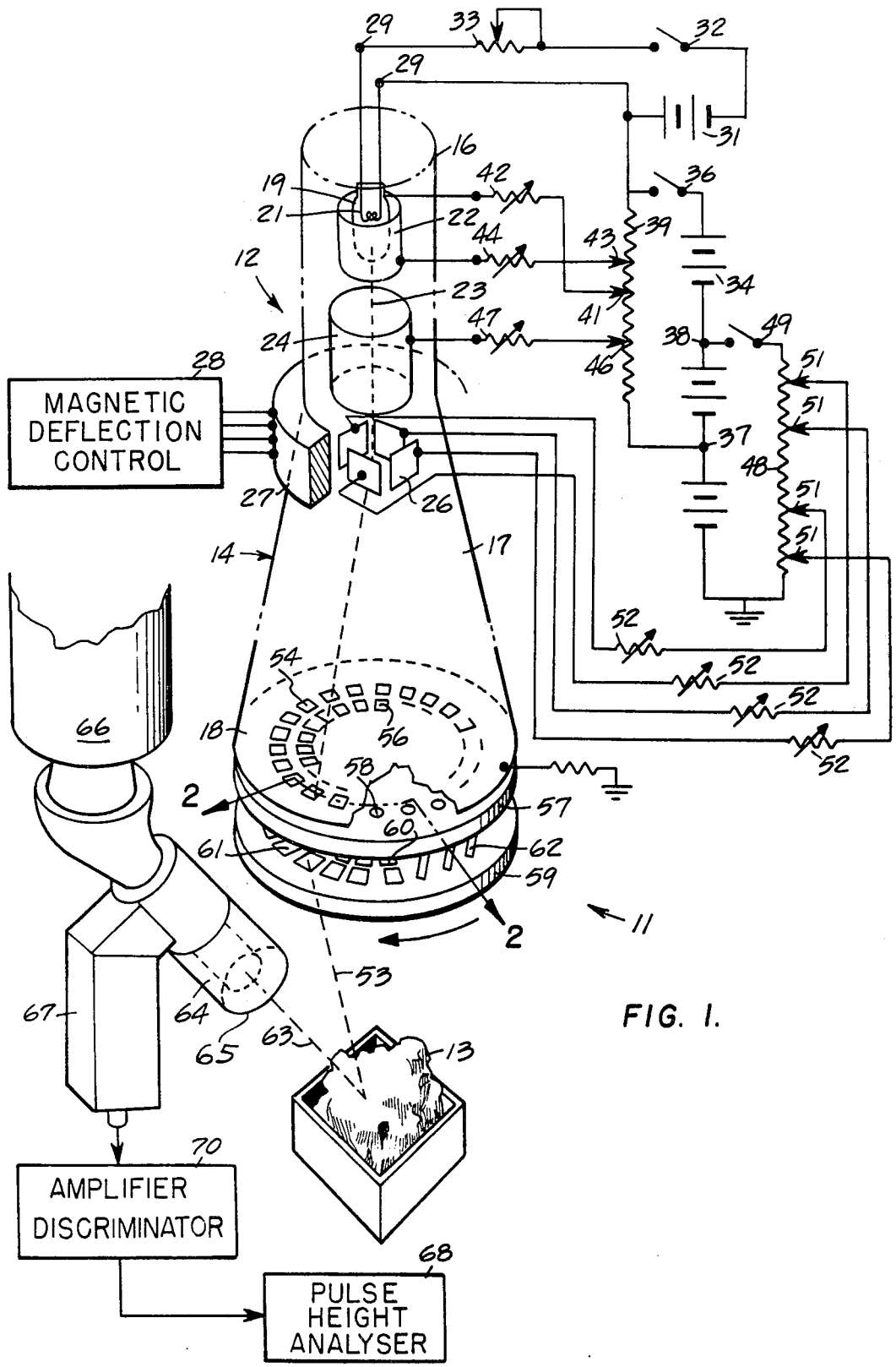
FIG. 1 is a schematic view of a first embodiment of an X-ray spectrometer in accordance with the invention.

The present invention will best be understood by first briefly reviewing certain properties of materials subjected to X-ray irradiation. Specifically, most chemical elements will fluoresce an X-ray spectrum having one or more specific wavelengths upon being irradiated by X-rays that do not necessarily include the same wavelengths and which may be a polychromatic mixture of many different wavelengths. Further, each of the known elements fluoresces a specific wavelength or combination thereof which is unique to that element and which differs from the fluorescent radiation of each other element. If a sample composed of a single element is subjected to polychromatic X-rays, the fluorescence from the sample can be detected and analyzed to produce a plot of the amount of X-ray fluorescence at each wavelength. This fluorescent X-ray spectrum is unique for that element and enables ready identification. If the sample is composed of a mixture of elements, a more complex fluorescent X-ray spectrum will be obtained, but it is possible in most instances to analyze the various peaks appearing in the spectrum to determine which elements are present and it is further possible to determine the relative amounts of each element from the relative heights of the peaks representative of each element. This process is termed "X-ray fluorescence analysis" and is potentially a very valuable assay technique. It is nondestructive of the sample and does not require any mechanical disruption thereof.

Accuracy and speed of X-ray fluorescence analysis are dependent upon the extent to which X-ray fluorescence from the sample can be maximized in relation to the background radiation of various wavelengths. The lack of suitable apparatus and techniques for optimizing X-ray fluorescence from elements suspected to be present in a sample has heretofore restricted the use of this potentially valuable assay technique.

While the wavelength spectrum of the X-rays which are impinged upon the sample does not determine the wavelengths of the fluorescence from the sample, there is a strong relationship insofar as the intensity of sample fluorescence is concerned. A different wavelength spectra may be required to maximize fluorescence from each particular element which may be present in the sample.

Accordingly, the present invention greatly facilitates accuracy, sensitivity, convenience, and speed of X-ray fluorescence analysis by providing a source of X-rays for sequentially irradiating a sample with selected ones of a large number of predetermined wavelength spectra. A practical, convenient source for exciting X-rays of selectable wavelength suitable for this purpose has not heretofore been available. In the conventional X-ray tubes or sources, high-energy electrons are caused to strike a target and the resulting X-rays have two distinct components. The first component is the characteristic fluorescent X-ray wavelengths of the particular element of which the target is composed and the other is a continuous wavelength distribution called "bremmstrahlung". While the wavelength of the characteristic X-rays from the conventional tube depends solely on the atomic number of the anode element, the bremmstrahlung wavelength mixture is strongly affected by the energy of the electron beam. This invention provides an X-ray source having a plurality of targets of differing composition to selectively produce any of a large number of characteristic X-ray wavelengths together with means for suppressing bremmstrahlung radiation so that a substantially pure output of any of a number of specific wavelength spectra may be obtained.

This greatly enhances the utility of X-ray fluorescence analysis as an assay procedure. Specifically, the sample may be initially irradiated with a polychromatic X-ray spectrum. The resulting fluorescence from the sample may then be detected and analyzed to produce a fluorescent X-ray spectrum, containing peaks at specific wavelengths, that enables a tentative identification of the probable elements in the sample. The X-ray source may then be adjusted to irradiate the sample with the specific X-ray wavelengths which will optimize fluorescence from those particular elements to confirm the presence of each such element and to determine the amount thereof in a rapid and accurate manner.

Preferably, detection and identification of the specific wavelengths in the X-ray fluorescence from the sample are performed by the energy dispersive technique in which the electric charge produced when a fluorescent X-ray from the sample is absorbed in a detector is measured. The collected charge, on a capacitor or the like, produces a readily measurable voltage which is proportional to the energy of the absorbed X-ray. This energy is inversely proportional to the wavelength of the X-ray thereby enabling determination of the wavelength.

Referring now to FIG. 1, an X-ray spectrometer system 11 is shown in schematic form including an X-ray tube or source 12 capable of irradiating a sample 13 which is to be analyzed with X-rays having any selected one of a large number of predetermined different specific wavelengths or combinations of specific wavelengths. Source 12 in this example has an evacuated envelope 14 with a relatively narrow cylindrical neck portion 16 formed of insulative material and a flared anode end portion 17, formed of conductive material, that terminates in a circular conductive end anode 18. Electron beam generating and deflection means are situated in the neck portion 16 of the envelope and may be essentially similar to those employed in cathode ray tubes. This may include an annular cathode 19 heated by a filament 21 and an annular control electrode 22 disposed coaxially therewith and extending slightly further toward the anode end of the envelope whereby the voltage applied to the control electrode will determine the current or intensity of the electron beam 23 emitted from the cathode. Electron beam 23 is focussed and accelerated by passage through an annular first anode 24 and then passes through a region bounded by four deflection plates 26 to which voltages may be applied to direct the beam toward any selected area of end anode 18. A magnetic beam deflection yoke 27, having control means 28, may be disposed around the envelope 14 in the region of deflection plates 26 to provide an alternate or supplemental means of controlling the direction of the electron beam, suitable detailed constructions for such magnetic deflection means and controls being well known in the art. Although not shown, it will be understood that various known provisions for enhancing beam focusing and tube life, such as ion traps, getter materials, magnetic focusing means, and the like, may be employed in the envelope 14 if desired.

In a preferred arrangement, the cathode 19 is at a high negative potential while end anode plate 18 is at ground to reduce the likelihood of arcing to nearby grounded structure. Filament terminals 29 are connected across a filament power supply 31 through a filament power control switch 32 and a variable resistor 33 that provides for adjustment of filament current. Although other circuit configurations are suitable, voltages for the electrodes 22, 24, and deflection plates 26 may be provided from a high-voltage power supply 34 having the positive side grounded and having the negative side coupled to one of the filament terminals 29 through a switch 36 and further having a pair of intermediate taps 37 and 38 of progressively more negative voltages. To provide voltages for the electrodes 19, 22, 24, the resistive element 39 of a first potentiometer is connected between tap 37 and switch 36. A first sliding contact 41 at resistive element 39 is coupled to cathode 19 through an adjustable current limiting resistor 42. A second sliding contact 43 is connected to control electrode 22 through an adjustable current limiting resistor 44 and a third sliding contact 46 is connected to first anode 24 through an adjustable resistor 47. The sliding contacts 41, 43, and 46 enable the voltages applied to cathode 19, control electrode 22, and first anode 24 to be selectively varied to determine beam current, energy, and focus.

To enable adjustment of the voltages applied to the deflection plates 26 for the purpose of controlling the direction of the electron beam 23, the resistive element 48 of a second potentiometer has one end grounded and the other end connected to power supply tap 38 through a deflector voltage on/off switch 49. Four adjustable sliding contacts 51 at resistive element 48 each connect with a separate one of the deflection plates 26 through a separate one of a plurality of adjustable current-limiting resistors 52. Accordingly, the voltage applied to each of the deflection plates may be individually varied to direct the electron beam 23 toward any selected area of the end anode plate 18.

Considering now means by which a secondary X-ray output 53 having a selectable one of a large number of predetermined wavelength spectra can be directed to the sample 13, a series of primary targets 54 are mounted in the end anode plate 18 in a circular array in this instance. An inner ring of similar primary targets 56 is also provided for purposes which will hereinafter be described. The primary targets 54 are composed of a number of different chemical elements and have sufficient thickness to completely stop the electrons of beam 23 and at least a portion of the primary targets have sufficient thickness to absorb much of the bremmstrahlung arising from the electron impact on the target. Where substantial bremmstrahlung absorption is desired, nickel, copper or iron primary targets in thicknesses of about $5 \times 10^{-3}$ cm. are typical for electron beam energies of less than about 40 KeV. Thin window supports may be provided for the targets 54 if necessary.

When the electron beam 23 is impinged upon a selected one of the primary targets 54, the target emits primary X-rays which include both the characteristic wavelength of the target element and considerable bremmstrahlung or polychromatic X-rays. Much of the bremmstrahlung is absorbed in passage through the primary target except in the case of certain specialized ones thereof which will be hereinafter described. Characteristic X-ray wavelengths are emitted by fluorescence from the opposite side of the selected primary target 54 which fluorescent X-rays may be accompanied by any unabsorbed bremmstrahlung.

Disposed adjacent end anode 18 is a collimator 57 formed of dense X-ray absorbant material and having collimation passages 58 therethrough with one such passage being adjacent each primary target 54 and 56. Disposed on the opposite side of collimator 57 from the primary targets 54 is a secondary target table 59 which may be rotated relative to the end anode 18 and collimator 57. A circular outer array of secondary targets 61 and matching inner array of secondary targets 60 are mounted on table 59, the secondary targets each being formed of different elements which fluoresce different specific wavelengths.

Table 59 is rotatable to enable any selected one of the secondary targets 61 to be moved into alignment with any selected one of the primary targets 54 so that the primary X-rays produced at any particular primary target can be transmitted to any selected one of the secondary targets 61. Collimator 57 serves to prevent primary radiation from a particular selected target 54 from reaching any secondary target 61 other than the selected one.

Upon irradiation by primary X-rays from a selected one of the primary targets 54, the selected secondary target 61 fluoresces the specific characteristic wavelength spectrum of the element of which the secondary target is composed. Depending on the particular element and target thickness, this may be substantially monochromatic or it may include several specific wavelengths. Any remaining bremmstrahlung in the primary X-rays is largely absorbed in the secondary target, the thickness of which is selected to accomplish this purpose. A thickness of about $1 \times 10^{-2}$ cm is typical for a molybdenum secondary target, for example, in a system where the electron beam 23 has an energy of about 40 KeV and substantial bremmstrahlung absorption is desired.

Upon irradiation by the fluorescent secondary X-rays 53 from a selected secondary target 61, the sample 13 to be analyzed in turn emits fluorescent X-rays 63. X-rays 63 have wavelengths characteristic of the elements of which the sample is composed and have relative intensities indicative of the proportion of each element therein. The fluorescent X-rays 63 from the sample are received at a sample detector 64. In this example, detector 64 is a liquid nitrogen cooled, solid-state detector, although spark chambers, gas-filled proportional counters, liquid Xenon proportional counters, or scintillator-photomultiplier detectors may also be employed. Detector 64 may be protected from X-ray tube and other background radiation by a shield. In the present example, liquid nitrogen cooling for detector 64 is provided by a cryostat 66. The output of solid-state detector 64 is coupled to a preamplifier 67 which amplifies the X-ray count for transmission to a pulseheight analyzer 68 or other count analyzing, recording or display means through a pulse-shaping, linear amplifier and amplitude discriminator 70 which suppresses noise. The detector 64 is preferably of the energy-dispersive type which, in effect, produces an output pulse having an amplitude proportional to the electric charge produced when each X-ray is absorbed. This charge and thus the output voltage are proportional to the energy of the absorbed X-ray which energy is, in turn, inversely proportional to the wavelength of the X-ray. Thus, pulse height analyzer 68 is able to sort counts according to the wavelength of the initiating X-ray from the sample to identify which wavelengths are present and in what amounts. This is the information needed to determine the composition of sample 13 by X-ray fluorescence analysis as hereinbefore discussed.

The X-ray source 12 enhances speed, sensitivity, and precision of the assay of the sample 13 by enabling irradiation of the sample with any selected one of a large number of specific wavelengths and by providing the capability of sequentially subjecting the sample to a series of different wavelengths each selected to optimize sample fluorescence from a specific possible constituent element of the sample. This capability results from the ability to match any of a large number of primary targets 54 with any of a large number of secondary targets 61 in an arrangement which suppresses contamination by bremmstrahlung and unwanted characteristic radiation from the target and other materials.

Figure 2:
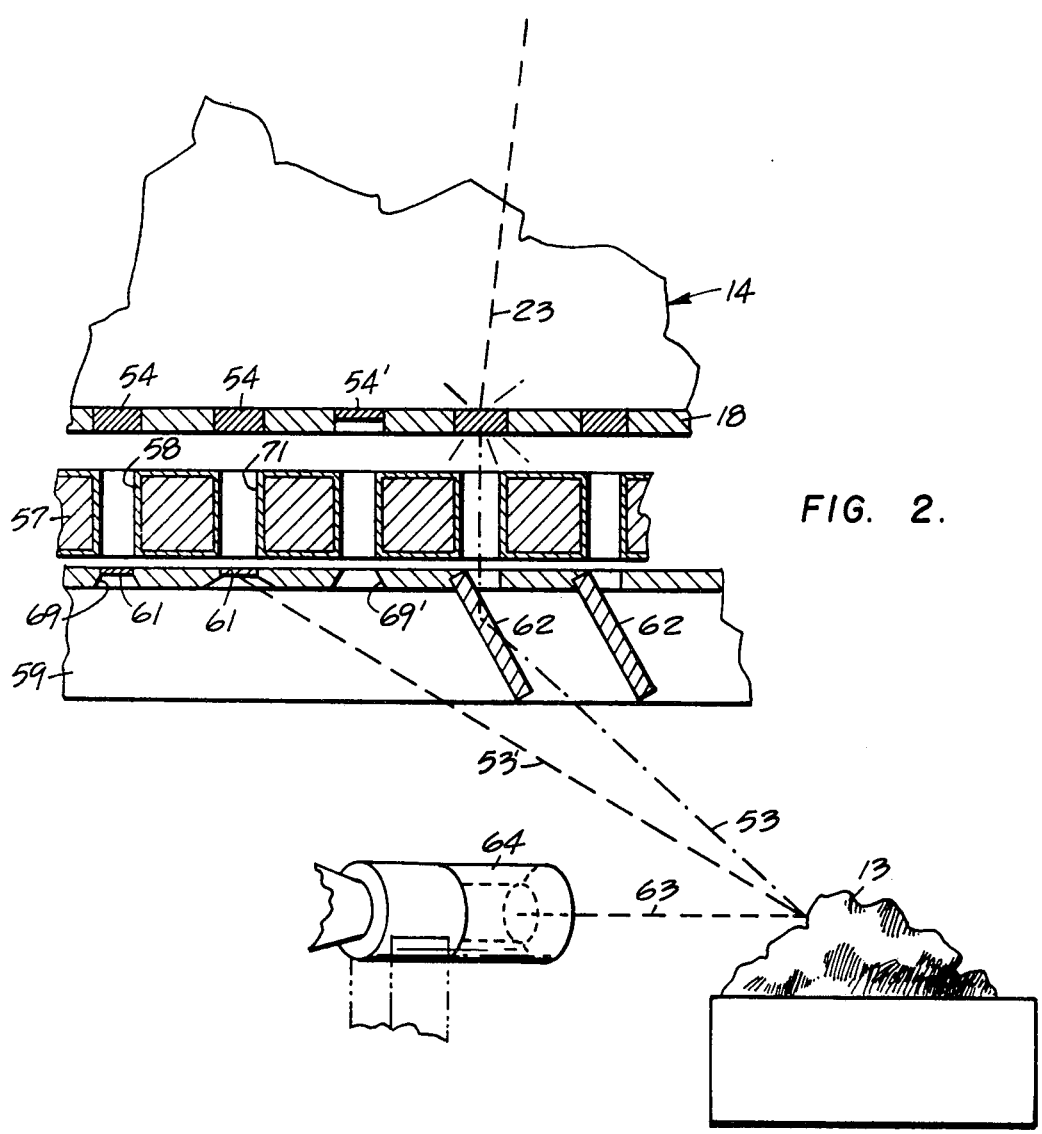
FIG. 2 is an enlarged schematic sectional view of a portion of the apparatus of FIG. 1 taken along curved line 2—2 thereof.

FIG. 2 illustrates more detail of the target and collimator structure and further illustrates useful variations in form and function for the primary and secondary targets which enable use of either forward or backward fluorescent X-ray emission from the secondary targets and which enable deliberate transmission of bremmstrahlung to the sample when that is desirable. In particular, the rotatable secondary target table 59 is provided with a series of apertures 69 in some of which secondary targets 61 are disposed transversely to the path of primary X-rays from the primary targets. Such secondary targets 61 make use of forwardly emitted X-ray fluorescence for the purpose of irradiating the sample 13. That is, the primary radiation from a primary target 54 strikes one surface of the secondary target 61 and, as illustrated by dashed line 53', the secondary X-ray output originates by fluorescence at the opposite side of the secondary target. However, a second group of secondary targets 62 may be provided in which the fluorescent secondary X-ray output 53 is emitted backwardly from the secondary target. For this purpose, the backward emission targets 62 are secured to table 59 in an oblique relationship to the axis of the adjacent collimator passage 58 through which primary X-rays arrive. As the secondary targets 62 depend on backward emission of fluorescent X-rays, such targets may be substantially thicker than targets 61 in order to absorb primary X-rays including bremmstrahlung arriving through the collimator passage 58. With respect to both types of secondary targets 61 and 62, it should be appreciated that fluorescent X-rays are emitted omnidirectionally and the dashed lines 53 and 53' simply represent that portion of the X-ray fluorescence which is directed toward the sample 13.

FIG. 2 illustrates certain other highly advantageous features of the target and collimator structure. For example, contamination of the secondary X-rays 53 output with with characteristic X-ray spectra from the material of the collimator 57 may be suppressed by coating the surfaces of the collimator, including passages 58, with a lining 71 of filtering material, such as beryllium, having a low atomic number. Considering still a further advantageous feature of the source construction, there may be instances, such as in the initial steps of an X-ray fluorescence analysis of a sample 13, wherein it is desired to produce a polychromatic X-ray output. While this can be done by cycling the electron beam 23 across a variety of the primary targets 54 in combination with a variety of the secondary targets 61 and 62, it is also provided for in this example of the invention by omitting any secondary target from one of the apertures 69' in rotatable table 59. Thus, bremmstrahlung from a primary target 54 in alignment with the open aperture 69' is not absorbed but is transmitted outward in the direction of the sample. Bremmstrahlung production may be enhanced if a particular one of the primary targets 54' is made of reduced thickness or replaced with a thin window for use in conjunction with the opening 69' in rotatable table 59. It should also be observed that one or more of the secondary targets may have thickness selected to cause such targets to act as filters, suppressing all but desired specific wavelengths, rather than acting to generate the secondary X-rays by fluorescence. Similarly, identical primary or secondary targets may be provided at spaced locations around the anode 18 and table 69 to provide for irradiation of sample 13 from different directions with a specific selected wavelength.

Figure 3:
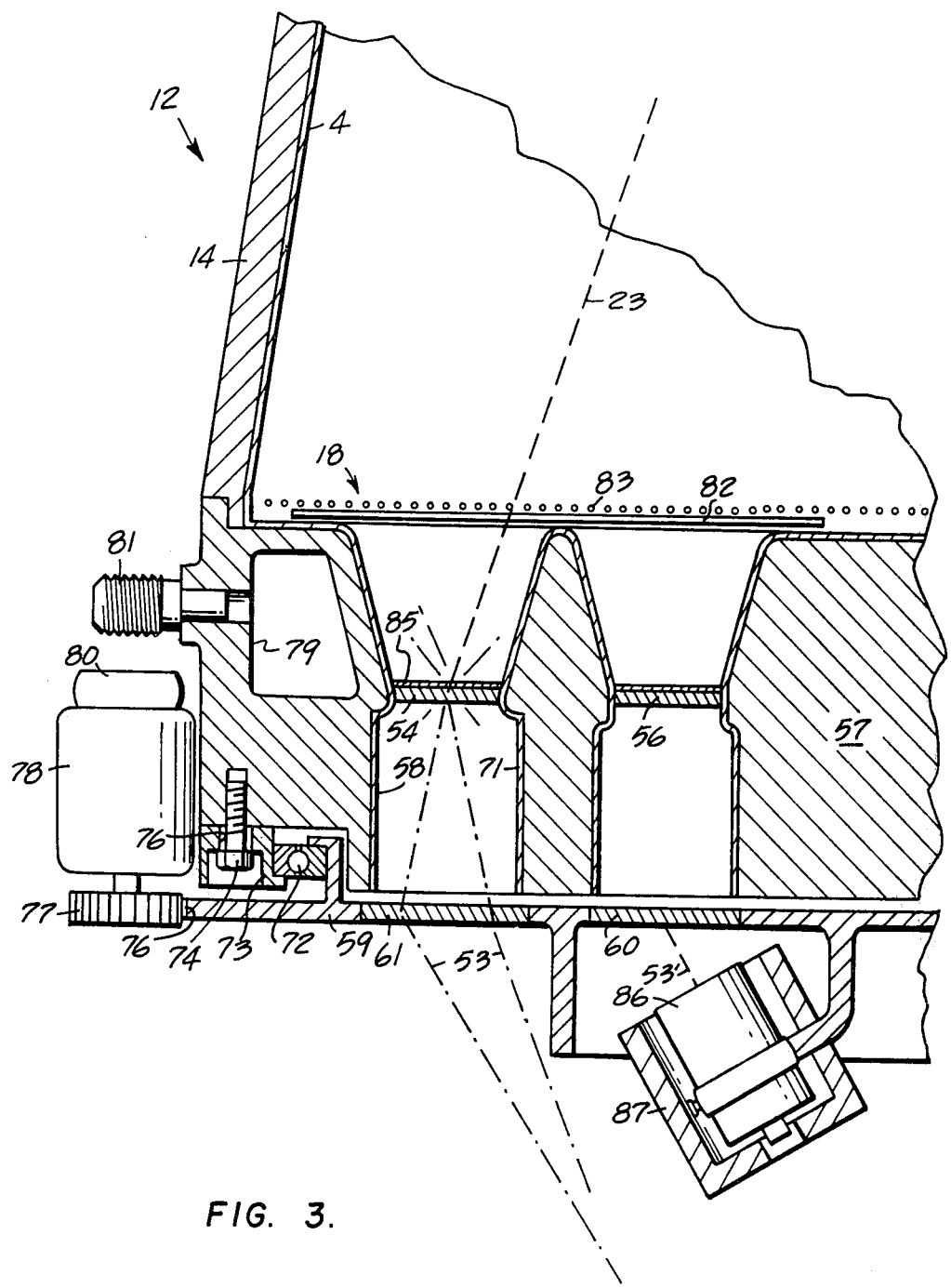
FIG. 3 is a partial cross-sectional view of a portion of the X-ray source of the spectrometer of FIG. 1 showing one example of structural detail for such source.

Certain structural details were omitted from FIGS. 1 and 2 in order to better illustrate certain basic principles of the invention. While the detailed construction of the apparatus may take a variety of forms, FIG. 3 illustrates one advantageous detailed construction of the target and collimator region of the X-ray source 12. Unlike FIG. 2, which is taken along on arc 2—2 of FIG. 1, FIG. 3 is a section view of a portion of the anode end of the X-ray source 12 taken along a radial plane thereof.

While the anode end 14 of the X-ray source 12, the collimator 57, and the rotatable table 59 may each be mechanically separate elements as depicted schematically in the preceding figures, such components may also be advantageously combined into a single assembly as shown in FIG. 3. Thus, the collimator 57 may be joined to the end of envelope 14 to form an end closure therefor. Rotatable table 59 carrying the secondary targets 60 and 61 may be attached to the collimator structure 57 through a bearing 72 and annular retainer 73 attached to the collimator by means such as screws 74. Preferably, the passages 76 in retainer 73 through which the screws 74 extend are of greater diameter than the screws so that the retainer and thus the rotatable table 59, including secondary targets 60 and 61, may be shifted laterally as necessary to bring the targets into optimum alignment with the collimation passages 58.

To provide for selective turning of the table 59 in order to bring a particular secondary target into alignment with a particular primary target, the edge of the table may be provided with gear teeth 76 which engage an output gear 77 of a servomotor 78 mounted on the collimator structure 57. Servomotor 78 carries a position sensing means 80 which will hereinafter be described.

Passages 58 of the collimator including the lining 71 thereof are outwardly flared toward the interior of envelope 14 and the primary target 54 associated with each such passage is disposed transversely therein at the small diameter portion of the flared section. The primary targets 54 and 56, having the thicknesses hereinbefore described, may be adequately cooled by heat conduction to the adjacent supporting surfaces if the electron beam 23 power is less than around 100 watts. If primary target thicknesses are insufficient for this purpose or higher electron beam power is utilized, suitable coolant passages 79 may be provided within the collimator 57 with fittings 81 being provided at the exterior surface to provide for a forced flow of coolant.

The above-described disposition of the primary targets 54 and 56 within flared extensions of the collimator passages 58 serves to suppress cross-contamination of adjacent primary targets from evaporated and redeposited target material which may otherwise result from impingement of an electron beam thereon. In the absence of this corrective provision, the material of one target may tend to be deposited on another thereby interfering with proper operation of the source. Cross-contamination may be still further suppressed by a coating 85 of carbon or other low atomic number material on the target and by extending a thin foil 82, supported by a wire grid 83, across the inner surface of collimator 57. Provided the foil 82 and grid 83 are thin and formed of a suitable low atomic number material, such as carbon for the foil and beryllium for the grid, the electron beam 23 loses little energy in passing through such structure and no significant undesired X-ray background is generated.

Considering now still another advantageous aspect of the X-ray source as depicted in FIG. 3, it is desirable in many operations to check the intensity of the secondary radiation flux 53 at the output of the X-ray source 12 at a particular time when a particular combination of primary and secondary targets and electron beam voltages is being used and it may also be desirable to monitor the wavelength spectrum of such radiation flux. The previously described inner arrays of primary targets 56 and secondary targets 60 are utilized for this purpose. If, at a given time, the electron beam 23 is being directed to a specific one of the primary targets 54, as depicted in FIG. 3, and it is desired to monitor secondary output flux or wavelength or both, the electron beam may be temporarily redirected to the associated inner one of the primary targets 56 or to other primary targets 56. This will cause a similar fluorescent X-ray output 53″ at the associated one of the inner secondary targets 60. A monitor detector 86, which may typically be a gas-filled proportional counter, is secured to rotatable table 59 adjacent each inner secondary target 60 in position to receive the fluorescent X-ray emission therefrom, the counter being preferably partially enclosed by a shield 87 to screen out background radiation other than that originating from the adjacent surface of the associated one of the secondary targets 60. The output of each monitor detector 86 may be processed essentially similarly to the output of the sample fluorescence detector 64 of FIG. 1 to obtain the desired data or may be utilized in automatic control of the spectrometer as will hereinafter be described.

Figure 4:
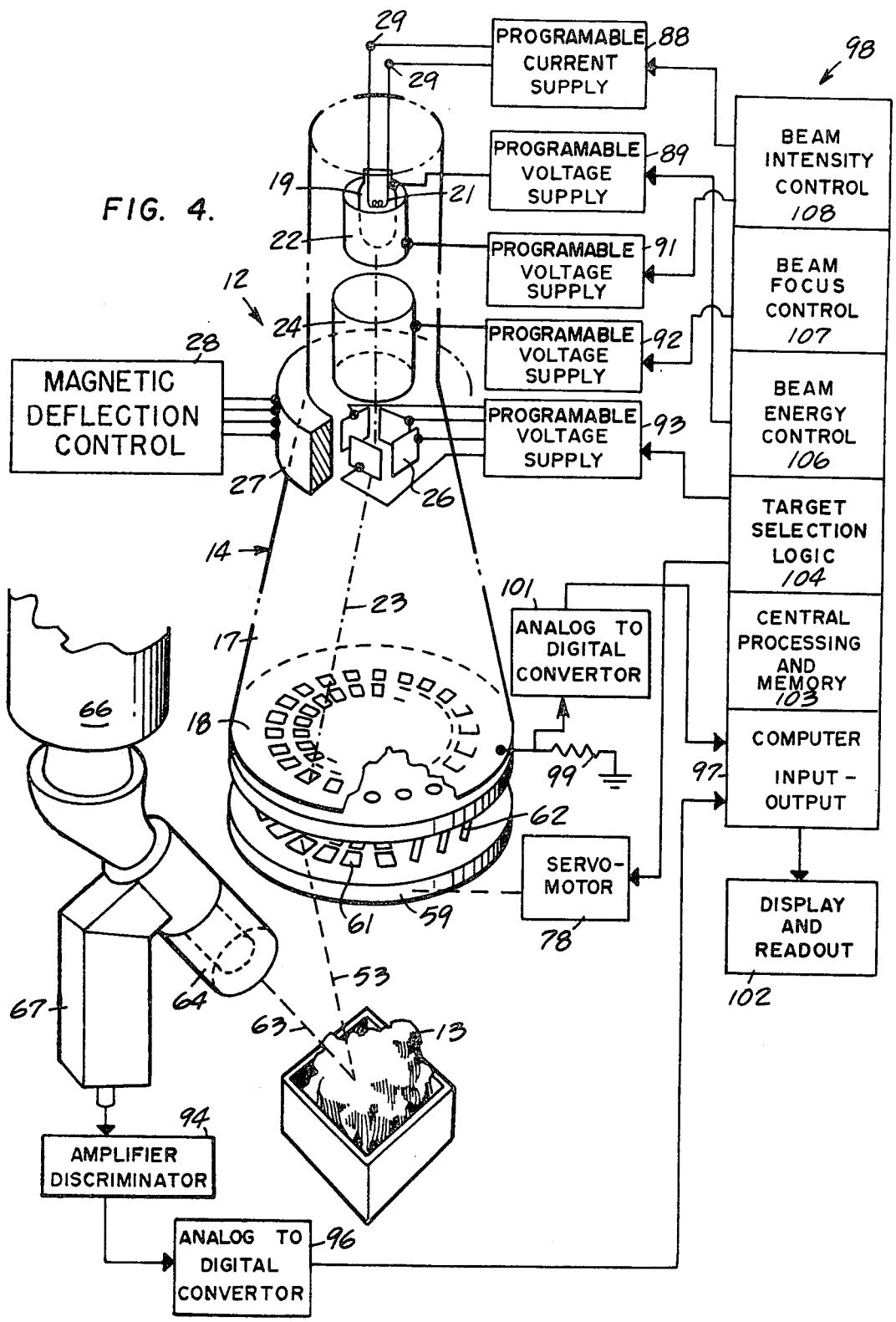
FIG. 4 is a schematic view of a modification of the X-ray spectrometer system including, in schematic form, a self-cycling feedback circuit for controlling the X-ray source to perform an analysis of a substance in an automatic manner or for other purposes.

FIG. 4 illustrates, in block form, modifications which enable self-cycling of the system to perform an X-ray fluorescence analysis of a sample 13, including automatic determination of the optimum X-ray output wavelengths from source 12 for the particular sample 13 and automatic control of the source to select the appropriate primary and secondary targets and electron beam intensities and energies.

For this purpose, the filament terminals 29 may be coupled to the output of a programmable current supply 88 of the known form which provides an output current having a magnitude determined by coded digital signals applied to the input. Similarly, the cathode 19 is coupled to the output of a programmable voltage supply 89 of the known form which supplies an output voltage selectively variable in response to coded input signals. Additional programmable voltage supplies 91, 92 and 93 are coupled to the control electrode 22, first anode 24, and deflection plates 26, respectively.

Output counts from sample X-ray fluorescence detector 64, after passage through the preamplifier 67, are applied to an additional amplifier-discriminator 94 and then to an analog-to-digital converter 96 of the known form which generates a binary digital output signal coded to indicate the height or amplitude of each such pulse. Thus, the output of analog-to-digital converter 96 consists of successive signals indicative of the wavelengths of counts from sample detector 64 and may be transmitted to the input 97 of a digital computer 98, preferably of the minicomputer form. The number of counts from detector 64 of a given wavelength occurring in a given interval of time is proportional not only to the amount of a particular chemical element in the sample 13, but also is proportional to the electron beam 23 current in source 12. Thus, to interpret the detector 64 output accurately and to control electron beam intensity, the computer must also be provided with digital input signals indicative of beam current. For this purpose, a low value resistor 99 is disposed in the ground connection to end anode plate 18 and the voltage developed across the resistor, which is proportional to the electron beam 23 current, is applied to another analog-to-digital converter 101. The output of converter 101 is coupled to the computer input 97 to transmit digital signals thereto coded to indicate electron beam current.

Given this capability of enabling the computer 98 to receive digital data indicative of X-ray counts at detector 64 and indicative of electron beam current and given the above described means for controlling the filament 21 current and the voltages applied to cathode 19, control electrode 22, first anode 24 and deflection plates 26 and given control of servomotor 78, by means to be hereinafter described in more detail, suitable programming of the computer 98 to perform the X-ray fluorescence analysis process as hereinbefore described will be apparent to those skilled in the art. A digital computer may readily be programmed to perform the logical operations which are required for the sample analysis and which are required to issue appropriate instructions, derived from such analysis at each stage of the process, to the programmable current and voltage supplies 88, 89, 91, 92 and 93 and to servomotor 78. By techniques well known to the art, the computer may also be caused to display the results of the analysis on an appropriate output device 102 which may include a visual display and a printout if desired. Depending on the choice of output means 102, the qualitative and quantitative assay results may be displayed in graphical or alphanumeric form on a cathode ray tube or may be printed out or plotted graphically. Such programming involves storing instructions in a central processing and memory unit 103 of the computer for selecting X-ray wavelengths for sample radiation. These instructions are executed by a target selection logic portion 104 of the memory which transmits digital control signals to programmable voltage supply 93 and to servomotor 78 in order to direct the electron beam 23 to the selected primary target and to rotate table 59 to align the selected second target therewith (or to align no secondary target therewith). Similarly, instructions are stored in a beam energy control portion 106 of the computer memory to transmit digital signals to programmable voltage supply 89 of the cathode to maintain a selected beam accelerating voltage. Still another portion 107 of the computer memory is provided with instructions to control programmable voltage supplies 91 and 92 for optimum beam focus and another portion 108 of the memory stores instructions for selecting optimum filament current and control electrode voltage and for transmitting correspondingly coded signals to programmable supplies 88 and 91.

It will be apparent that if the programmable current and voltage supplies 88, 89, 91, 92 and 93 are of the form requiring analog inputs, then digital-to-analog converters may be situated in the signal paths between each such supply and the computer 98.

While the system of FIG. 4 has been described as utilizing the electrostatic deflection plates 26 for the purpose of directing the electron beam 23, it will be apparent that similar techniques may be utilized to control the magnetic deflection system 28 either alternately or in conjunction with the electrostatic deflection plates.

Figure 5A:
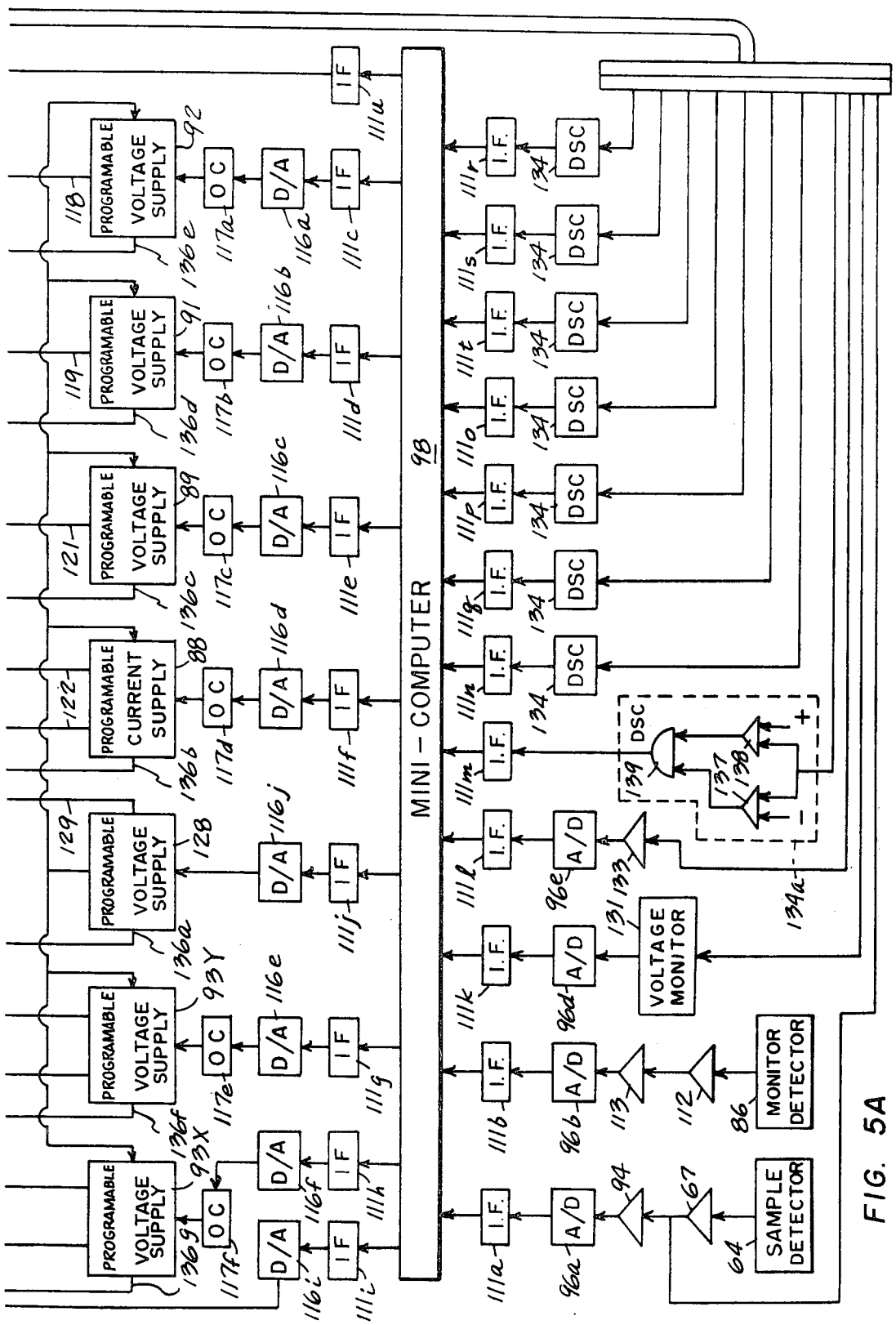
FIGS. 5A and 5B, which may be juxtaposed with FIG. 5B above FIG. 5A to form a single continuous circuit diagram, illustrates the circuit of FIG. 4 in greater detail.
Figure 5B:
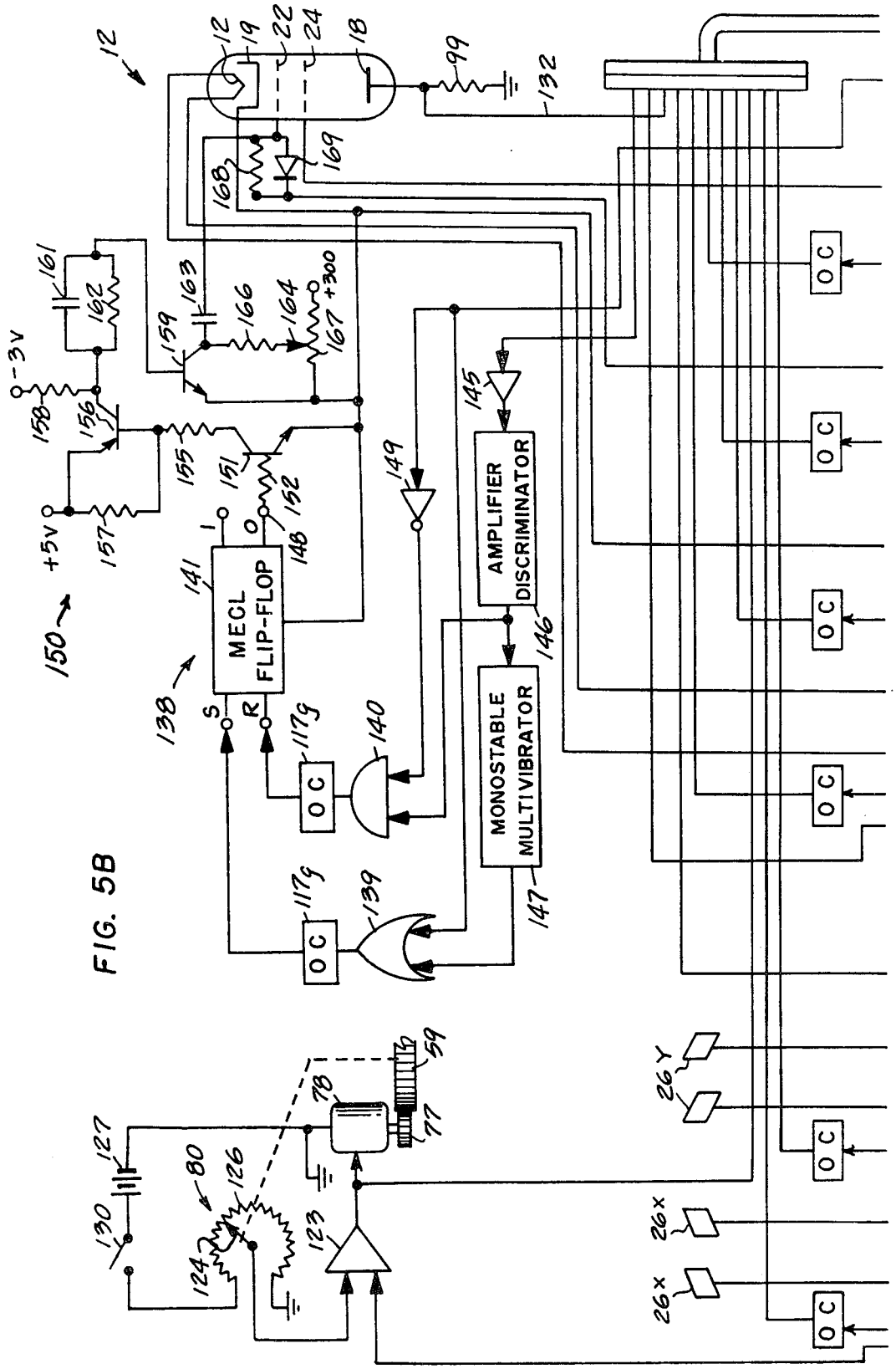

Circuit provisions for adapting the system of FIGS. 1 to 4 to automatic or self-cycling operation with the aid of a computer are shown in more detail in FIGS. 5A and 5B. FIG. 5A may be disposed with FIG. 5B immediately above FIG. 5A to form a single continuous circuit diagram. In FIGS. 5A and 5B, the legends "A/D" and "D/A" refer respectively to analog-to-digital and digital-to-analog converter circuits, suitable detailed constructions therefor being known to the art. Similarly, the legend "IF" refers to interface cards, also known to the art, for connecting digital signal channels of external circuitry with a computer. If, for example, the computer 98 is a minicomputer of the form identified as PDP-11, manufactured by Digital Equipment Corporation, the interfaces IF may be of the DR11A form manufactured by the same company. The legend "OC" identifies optical coupling devices of the known form through which digital signals may be transmitted from one device to another without requiring direct electrical connection therebetween and which are used for isolation where the signal receiving circuit is at a high voltage level relative to the signal input circuit. The legend "DSC" refers to device status circuits of a form which will be hereinafter described.

Referring now to FIGS. 5A and 5B in conjunction, fluorescent X-ray counts from the previously described sample detector 64 are initially amplified by the preamplifier 67 and further amplified by amplifier 94 and then transmitted to the analog-to-digital signal converter 96 which codes each count signal according to pulse height for transmission to the computer 98 through an interface 111a. Accordingly, with suitable programming, the computer 98 is enabled to store a count of the number of fluorescent X-rays from the sample of each specific wavelength to establish the characteristic wavelength spectrum of fluorescent X-rays from the sample. Counts from the several monitor detectors 86, of which only one is depicted in FIG. 5, are similarly transmitted through a preamplifier 112, amplifier 113, analog-to-digital converter 96b, and interface 111b.

Computer 98 is enabled to control the first anode voltage at X-ray source 12 through an interface 111c, digital-to analog converter 116a, and optical coupler 117a which jointly form a control signal channel to the previously described programmable voltage supply 92. Supply 92 has a controlled voltage output 118 connected to the first anode 24 of the source. Similarly, the programmable voltage supply 91, having a controlled voltage output 119 coupled to the source control grid 22, is responsive to computer instructions received through an interface 111d, digital-to-analog converter 116b, and optical coupler 117b. Another interface 111e, digital-to-analog converter 116c, and optical coupler 117c enable the computer to control programmable voltage supply 89 which has a controlled voltage output 121 connected to the cathode 19 of the X-ray source 12. The computer is enabled to control the filament current of the source through an interface 111f, digital-to-analog converter 116d, and optical coupler 117d, the supply 88 having a pair of controlled current conductors 122 connected across the filament 21 of the source.

Control of electron beam deflection within the source 12 by the computer is enabled by an interface 111g, digital-to-analog converter 116e, and optical coupler 117e forming a control signal path to programmable voltage supply 93Y which has a pair of controlled voltage outputs connecting with a first pair of the opposed deflection plates 26Y. Similarly, an interface 111h connects with a digital-to-analog converter 116f which in turn connects through an optical coupler 117f with programmable voltage supply 93X which has a pair of controlled voltage outputs connected to the remaining pair of opposed deflection plates 26X, thus enabling primary target selection within source 12 by the computer.

To enable secondary target selecton, an interface 111*i* connects the computer with a digital-to-analog converter 116*i* having an output connected to one input of a comparator 123, the output of which is connected to servomotor 78 to supply operating current thereto. Accordingly, servomotor 78 will operate to rotate secondary target table 59 if there is an output from comparator 123. To enable the voltage level supplied to the comparator 123 from digital-to-analog converter 116*i* to determine the rotational position of table 59, the other input of the comparator is connected to a rotatable tap contact 124 which is turned by servomotor 28 in synchronism with table 59. Rotatable tap 124 is in sliding contact with a circular resistor 126 having a DC voltage source 127 connected thereacross in series with an on/-off switch 130. With switch 130 closed, the voltage at rotatable contact 124 is a function of the rotational position thereof and this voltage is supplied to the other input of comparator 123. The comparator 123 will produce an output, causing motor 78 to operate, until such time as rotation of the contact 124 brings the voltage applied to comparator 123 from contact 124 into balance with the control voltage applied thereto from digital-to-analog converter 116*i* at which point the output of the comparator ceases and motor rotation stops.

The basic reference voltage, between the high voltage end of X-ray source 12 and ground, with reference to which the several programmable supplies 88, 89, 91, 92 and 93 provide selected voltage variations, is itself determined by an additional main programmable voltage supply 128 having an output coupled to each of the other programmable supplies. Main supply 128 is itself controllable by instructions from computer 98 through an interface 111*j* and digital-to-analog converter 116*j*. No optical coupler is employed in the last described instruction channel, as the main voltage supply 128 is of the known form having internal means providing isolation of the output from the signal receiving input components which operate at relatively low voltages.

In order to control the X-ray source 12 and servomotor 78 to obtain optimum speed and accuracy of the sample analysis, it may be desirable to provide the computer 98 with certain additional input information for reference purposes. For example, the computer may be enabled to monitor various significant source operating voltages to determine if these conform with the instructions issued by the computer and to enable corrective modifications in instructions if needed. For this purpose, the main programmable voltage supply 128 has a monitor output 129 which is coupled to a voltage monitor 131. The output of monitor 131 is transmitted to the computer through an analog-to-digital converter 96*d* and interface 111*k*. Similarly, a voltage signal indicative of electron beam current within the X-ray source 12 is provided to the computer through a conductor 132 connected between end anode 118 and an amplifier 133 having an output coupled to analog-to-digital converter 96*e* which in turn provides the digitized beam current information to the computer through an interface 111*l*.

To inform the computer if any of the outputs of the several programmable voltage and current supplies or the servomotor control comparator 123 are out of conformity with the instructions being applied thereto, which condition occurs momentarily following a change of instructions, a series of device status circuits 134 are employed. A first such device status circuit 134*a* detects any departure of the output voltage of the main programmable voltage supply 128 from that indicated by the control signal currently being received from the associated digital-to-analog converter 116*j*. Programmable voltage supplies 128 of this form have an error signal output 136*a* on which a signal appears whenever there is a discrepancy between the input instructions and output voltage. Error signal terminal 136*a* is coupled to the input of the device status circuit 134*a* which has an output coupled to the computer through an interface 111*m*.

The device status circuit 134*a* has a pair of digital output comparators 137 and 138 each having the main voltage supply error signal 136 connected to one input. A small negative reference voltage is applied to the other input of one comparator 137 while a small positive reference voltage is applied to the other input of the other comparator 138. Thus, if the error signal from main voltage supply terminal 136*a* remains within the narrow limits defined by the small positive and negative voltages, the outputs of both comparators 137 and 138 are high. If the error signal increases significantly in either direction, the output of one of the comparators goes low. The outputs of the two comparators 137 and 138 are connected to the inputs of an AND gate 139, the output of which is coupled to the interface 111*m*. The output of the AND gate 139 is high when the received error signal is within the acceptable narrow limits and goes low to inform the computer when a significant degree of error is detected.

Similarly, the error signal outputs 136*b* and 136*g* of programmable supplies 88, 89, 91, 92, 93Y and 93X, respectively, are each coupled to a separate one of a series of device status circuit 134 which are in turn coupled to the computer 98 through interfaces 111*n*, 111*o*, 111*p*, 111*q*, 111*r*, and 111*s*, respectively. For similar purposes, the output of servomotor control comparator 123 connects with an additional device status circuit 134 and interface 111*t* to inform the computer when the secondary target table 59 is undergoing movement.

Speed and accuracy of the system can be greatly enhanced if the generation of X-rays by source 12 is temporarily interrupted during periods when any significant operating parameter is temporarily out of conformity with the instructions supplied by computer 98 and also during the period required to process each X-ray count produced by sample detector 64. A source pulsing circuit 138 is provided for this purpose.

Pulsing circuit 138 utilizes an OR gate 139 and an AND gate 140 having outputs coupled respectively to the set and reset inputs of an MECL-type flip-flop 141 through optical coupler 117*g*. To reset the flip-flop upon detection of an X-ray by sample detector 64, the output of preamplifier 67 is coupled to one input of AND gate 140 through an isolating amplifier 145 and discriminator amplifier 146. As will hereinafter be described in more detail, resetting of flip-flop 141 blocks X-ray production in source 12. To enable the computer to override the pulsing circuit 138 and maintain X-ray production when that is desirable, the other input of AND gate 140 is controllable by the computer through an interface 111*u* and inverter 149.

Setting of the flip-flop to restore X-ray production after a predetermined period sufficient to process a detected X-ray is accomplished through a connection from the output of amplifier 146 to one input of OR gate 139 through a time delay means such as a monostable multivibrator 147. The other input of OR gate 139 is coupled to the computer through interface 111u to enable the computer to maintain X-ray production when necessary by overriding the pulsing circuit 138.

A single one of the outputs of flip-flop 141 is utilized to control pulsing of the X-ray source 12, this being the output 148 which is high when the flip-flop is in the reset state indicating that a count has been detected or that one or more operating parameters are incorrect as described above. This high condition of flip-flop output 148 is caused to block temporarily the electron beam generation within source 12 by applying a negative voltage pulse to control grid 22 relative to cathode 19. For this purpose, the output voltage at flip-flop output terminal 148, which is unipolar, is amplified and made bipolar by a circuit 150.

Circuit 150 may be formed of a first transistor 151 having a base coupled to flip-flop output 148 through a resistor 152 and having an emitter coupled to cathode 19. The collector of transistor 151 is coupled to the base of a second transistor 156 through a resistor 155. A small positive voltage, typically 5 volts, is applied to the emitter of transistor 156 and is also applied to the base thereof through a resistor 157. A small negative voltage, typically −3 volts, is applied to the collector of transistor 156 through a resistor 158, the collector of transistor 156 being coupled to the base of a third transistor 159 through a speed-up filter circuit formed by a parallel capacitor 161 and resistor 162. The emitter of transistor 159 is coupled to cathode 19 while the collector thereof is coupled to control grid 22 through a capacitor 163. The collector of transistor 159 is also connected to the movable contact 164 of a potentiometer through a resistor 166. A positive voltage, typically +300 volts, is applied to the resistive element 167 of the potentiometer which has one end connected to cathode 19. The previously described connection of controlled voltage output 119 of programmable voltage supply 91 to control grid 22 is made through a resistor 168 and a diode 169 which is in parallel therewith for D.C. restoration. It should be understood that the voltages referred to in the foregoing description of circuit 149 are voltages taken relative to the basic high negative voltage at the cathode end of X-ray source 12 and are additive thereto rather than being relative to ground.

During the periods that an electron beam is being produced in source 12 to generate X-rays, output 148 of flip-flop 141 is low and thus transistor 151 is biased off and transistors 156 and 159 are also biased off. Under this condition, the voltage applied to control grid 22 is determined wholly by supply 91 and acts to draw electrons from cathode 19 to form the desired electron beam. Upon receipt of a reset pulse at flip-flop 141 from AND gate 140 indicating that a sample count is being processed, output 148 of the flip-flop goes high. Transistor 151 is turned on thereby turning on transistors 156 and 159. The resultant conduction through transistor 159 reduces the positive voltage on capacitor 163. This applies a negative step voltage at control grid 22 relative to cathode 19 thereby cutting off the electron beam within source 12. Upon setting of the flip-flop 141 by receipt of the delayed set pulse from OR gate 139, following expiration of a predetermined count processing time, flip-flop output 148 again goes low turning off transistor 151. This turns off transistors 156 and 159 to restore the original voltage relationship between control grid 22 and cathode 19 thereby regenerating the electron beam in the X-ray source 12.

Variations in the previously described configuration of the X-ray source 12, including the type and disposition of the primary and secondary targets therein, may readily be made. Referring now to FIG. 6, a modification of the geometry of the X-ray source 12a is shown in which backward emission of X-rays from both the primary targets 54a and secondary targets 61a is utilized and in which the sample 13a to be assayed is retained in a different manner. Specifically, the source 12a is designed to assay samples deposited on a cone of filter paper 171 which is received in a conforming cavity 172 formed coaxially in the end anode 18 of housing 14a. The primary targets 54a in this example are mounted in the interior wall of vacuum envelope 14a in cavities 173 therein in oblique relationship to the electron beam 23a whereby when primary X-rays 174, including bremmstrahlung and characteristic X-rays, are emitted toward passages 58a in a collimator end portion 57a of the housing from the same surface of the target that receives the electron beam. A thin foil and supporting grid structure 176 formed of low atomic number materials may be disposed across each cavity 173 to prevent cross-contamination between primary targets by evaporation, spalling, or the like. Where such protective means 176 are utilized, pump out channels 177 communicate the interior of envelope 14a with each cavity 173 to prevent creation of a pressure differential when the envelope is evacuated.

The primary X-rays 174 from the selected primary target 54a are transmitted through an associated one of the collimation passages 58a, each of which contains a thin window 178 of low atomic number material, such as beryllium, to impinge upon a selected one of the secondary targets 61a which has been positioned in alignment with the passage 58a. For this purpose, the secondary targets 61a may be carried upon a table 59a rotatable by a servomotor 78a as previously described.

The secondary targets 61a are also disposed obliquely with respect to the path of the primary X-rays 174 in position to intercept and absorb bremmstrahlung from the primary targets while emitting fluorescent secondary X-rays 53a, characteristic of the particular target material, toward the sample 13a. If desired, an X-ray filter 181 may be positioned in the path of the secondary X-rays 53a from the secondary target to the sample in order to suppress wavelengths other than a particular one with which it is desired to irradiate the sample. Suitable filter compositions for absorbing certain X-ray wavelengths while transmitting others are known to the art. Using the above-described geometry, the sample fluorescence detector 64a may be positioned on the axis of the source 12a in position to view the sample 13a through a circular window 182 provided in table 59a for that purpose. The monitor detectors 86a may be mounted on collimation structure 57a between collimator passages 58a and sample-receiving cavity 172.

Figure 7:
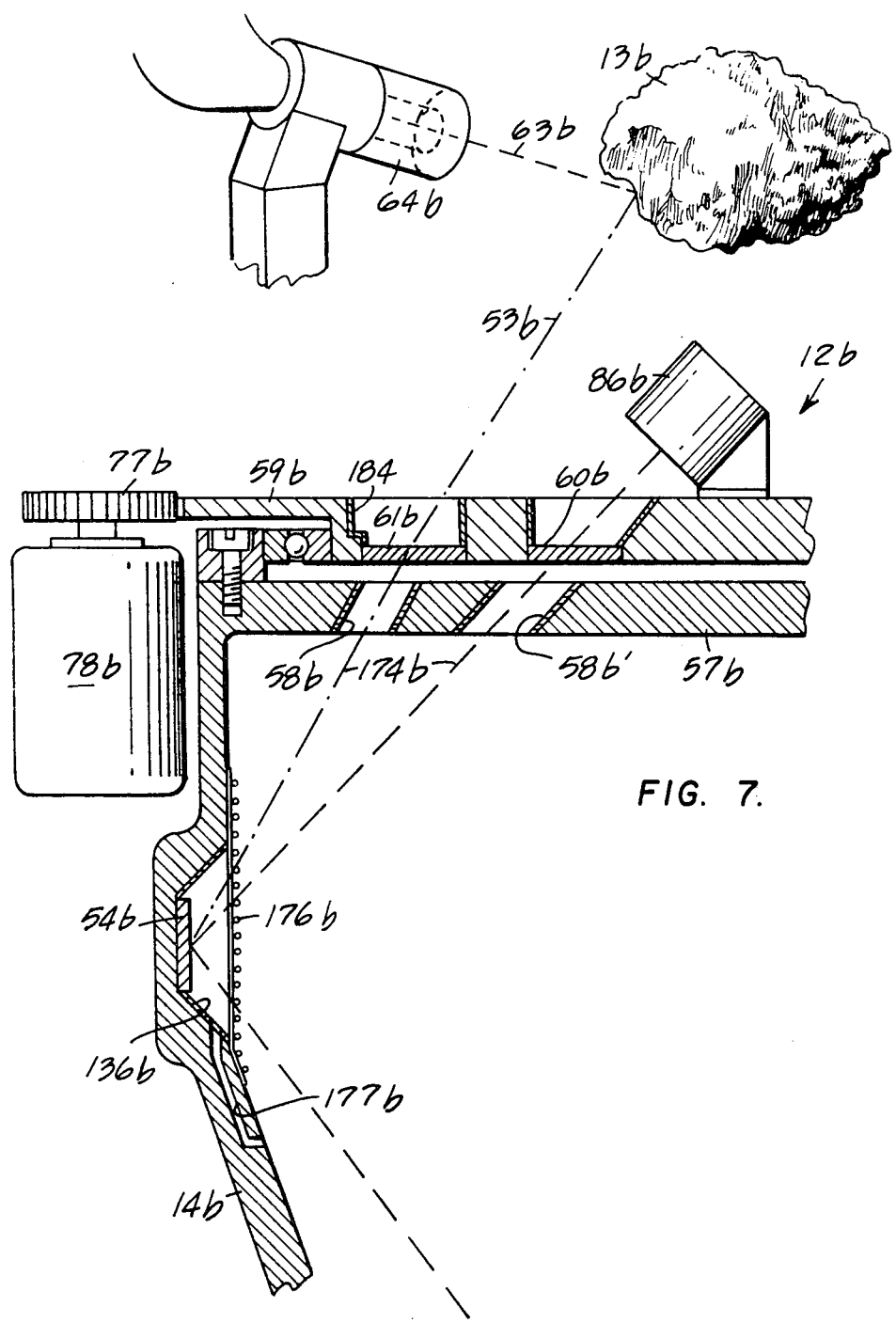
FIG. 7 illustrates another modification of the X-ray source.

Still another suitable geometry for the X-ray source 12b is illustrated in FIG. 7. This embodiment provides for backward angle X-ray emission from the primary targets 54b in conjunction with forward emission from the secondary targets 61b. The primary targets 54b may be mounted in cavities 173b in the sidewall of housing 14b in a manner similar to that described with reference to the preceding embodiment. Thus, a protective foil and grid 176b may be disposed across each cavity 173b and a pump out channel 177b communicates therewith.

Primary X-rays 174b from the selected primary target 54b are transmitted through a passage 58b in collimating structure 57b to impinge upon a selected one of the secondary targets 61b, each of which is mounted in a well 184 in a table 59b which may be rotated by a servomotor 78b as previously described. The secondary targets 61b are disposed transversely in the wells 184 so that secondary fluorescent X-rays 53b are emitted from the sie of the secondary target which is opposite from the side that receives the primary X-rays 174b. In this embodiment, the monitor detectors 86b may be mounted on table 59b in position to view secondary X-rays emitted from duplicate secondary targets 60b also carried on the table 59b in alignment with additional collimation passages 58b'.

Figure 8:
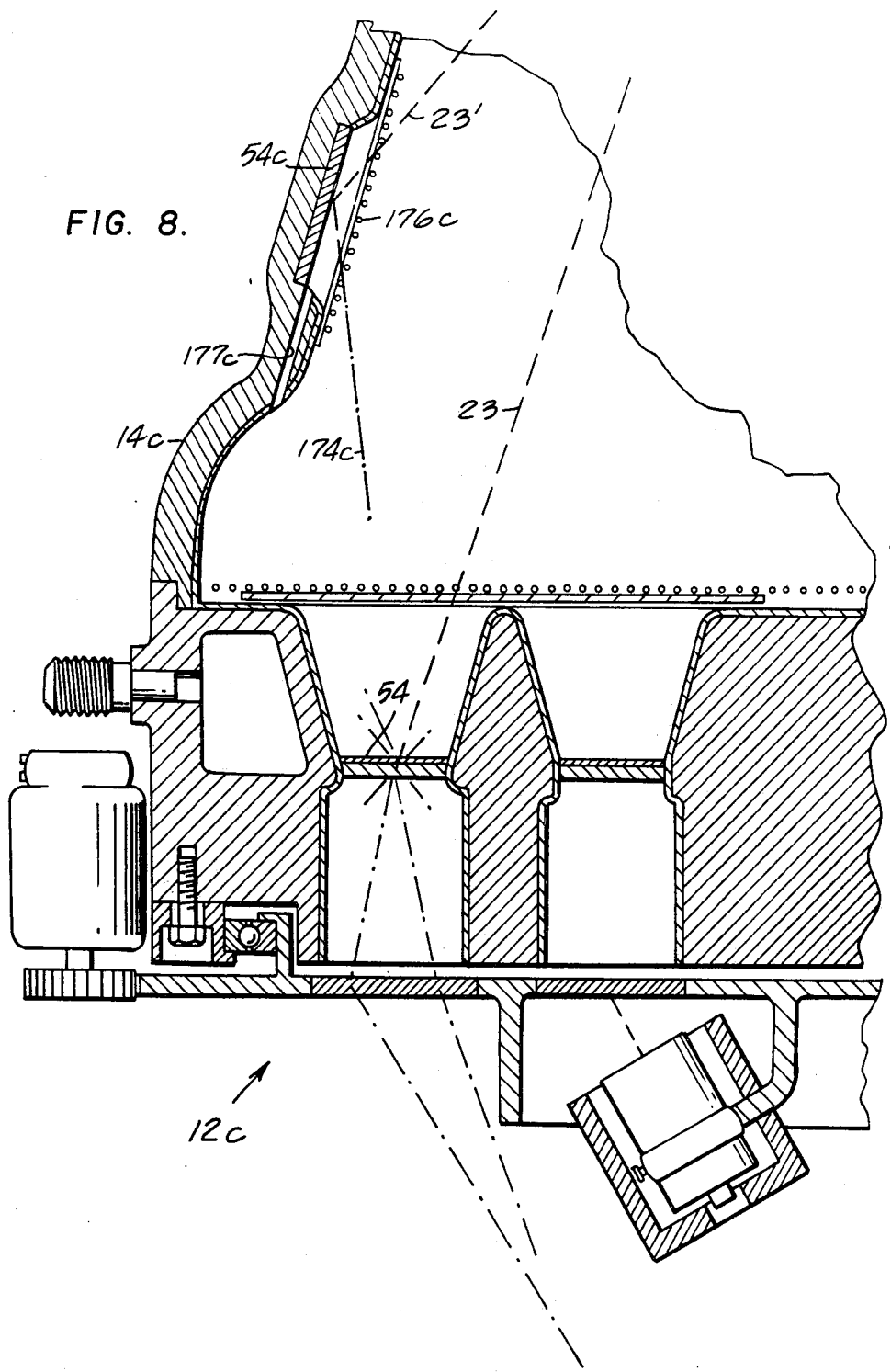
FIG. 8 illustrates still another variation of the X-ray source construction.

Certain of the previously described embodiments employ forward emission from one or both of the primary and secondary targets while others employ backward emission from one or both targets. Backward emission is defined as utilization of the X-rays emitted from the same surface of the target that receives the radiation which generates the X-rays while forward emission is defined as the utilization of X-rays emitted from the surface of the target opposite from that which receives the initiating radiation. In general, the choice between the several configurations depends primarily on whether wavelength purity or intensity of the output from the source needs to be emphasized. Backward emission provides greater intensity of the output radiation but, owing to the greater opportunity for scattering of bremmstrahlung, the output tends to be slightly more contaminated with undesired wavelengths than where forward emission is used. Where it is desired to provide a choice in a single X-ray source, provisions may be made to utilize either type of emission from either of the primary and secondary targets. The embodiment of the invention previously described with particular reference to FIG. 2 illustrated a construction providing for either forward or backward emission from the secondary targets 61 and 62. FIG. 8 illustrates still another modification wherein the choice of either forward or backward primary X-ray emission from the primary targets 54c is also provided.

The X-ray source 12c construction shown in FIG. 8 may be similar to that of FIG. 3 except for the providing of an additional set of primary targets 54c in the sidewall of vacuum envelope 14c. These additional targets 54c may be similar to those described with reference to FIGS. 6 and 7 and accordingly need not be redescribed. It will be apparent that the electron beam 23 may be selectively switched to any one of the additional primary targets 54c to produce primary X-rays 174c by backward emission where high intensity is desired or may be redirected to utilize the previously described primary targets 54 if the more strongly monochromatic output obtainable from forward emission is desired.

Thus, while the invention has been described with respect to certain preferred embodiments, it will be apparent that many modifications are possible and it is not intended to limit the invention except as defined by the following claims.

What is claimed is:

1. An X-ray fluorescence analysis spectrometer comprising:

an X-ray source having means for producing any selected one of a plurality of different specific predetermined X-ray spectra, said X-ray source having means for producing an accelerated charged particle beam and having at least one first primary target positioned to intercept said charged particle beam to produce primary X-rays in response to bombardment thereby and having a first plurality of spacedapart secondary targets each of different composition and means for directing said primary X-rays to any selected one of said secondary targets to produce secondary X-rays thereat which have different X-ray spectra at different ones of said secondary targets, means for supporting a substance to be analyzed in position to receive said X-rays produced by said selected ones of said secondary targets, an X-ray detector disposed for detecting characteristic fluorescent X-rays emitted from said substance in response to said irradiation thereof, and a self-cycling system coupled to said detector and to said X-ray source and having means for controlling said X-ray source to initially irradiate said substance with a polychromatic X-ray spectrum and means coupled to said detector for analyzing the wavelength spectrum of characteristic X-ray fluorescence from said substance in response to said polychromatic irradiation thereof to indentify wavelengths characteristic of specific elements, said self-cycling system further having logic circuit means controlling said X-ray source to sequentially irradiate said substance with a plurality of specific X-ray spectra each selected to cause strong X-ray fluorescence from a particular separate one of said specific elements, and further having means for registering a value having a magnitude proportional to the amount of characteristic fluorescent X-rays of each of said elements which are detected during said irradiation of said substance by said specific X-ray spectra.

2. The combination defined in claim 1 wherein a plurality of said first primary targets are provided in said X-ray source together with means for directing said charged particle beam to any selected one thereof, further comprising a second plurality of primary targets each having a composition similar to that of an associated separate one of said plurality of first primary targets, a second plurality of secondary targets each having a composition similar to that of an associated separate one of said first plurality of secondary targets, at least one monitor X-ray detector positioned to receive and detect secondary X-rays emitted from at least one of said second plurality of secondary targets, and wherein said self-cycling system has means for momentarily diverting said charged particles from a selected first primary target to the one of said second plurality of primary targets which is associated therewith to cause said monitor detector to produce a signal indicative of the radiation flux being directed to said sample and has means responsive to said monitor detector signal for adjusting the charged particle beam current if said detected radiation flux differs from a predetermined value.

3. The combination defined in claim 1 further comprising a second plurality of secondary targets each having a composition similar to that of an associated separate one of said first plurality of secondary targets, at least one monitor X-ray detector positioned to receive and detect secondary X-rays emitted from at least one of said second plurality of secondary targets to produe a signal indicative of the secondary radiation flux being directed to said sample and wherein said self-cycling system has means coupled to said monitor detector for adjusting the charged particle beam current if said detected radiation flux differs from a predetermined value.

* * * * *

UNITED STATES PATENT OFFICE
CERTIFICATE OF CORRECTION

Patent No. 4,048,496　　　　　　　　　Dated September 13, 1977

Inventor(s)　Richard D. Albert

It is certified that error appears in the above-identified patent and that said Letters Patent are hereby corrected as shown below:

Abstract, line 18 - "uncontrolled" should read --controlled--.

Signed and Sealed this

Fourth Day of April 1978

[SEAL]

Attest:

RUTH C. MASON
Attesting Officer

LUTRELLE F. PARKER
Acting Commissioner of Patents and Trademarks